United States Patent [19]

Deckner et al.

[11] Patent Number: 4,863,725

[45] Date of Patent: Sep. 5, 1989

[54] NOVEL CLEAR OIL-FREE MOISTURIZER COMPOSITION

[76] Inventors: George E. Deckner, 645 Hort St., Westfield, N.J. 07090; Hedwig O'Grady, 4 Cardinal Rd., Holmdel, N.J. 07733

[21] Appl. No.: 650,141

[22] Filed: Sep. 13, 1984

Related U.S. Application Data

[63] Continuation-in-part of Ser. No. 437,085, Oct. 27, 1982, abandoned.

[51] Int. Cl.$^4$ .......................... A61K 7/48; A61K 9/10
[52] U.S. Cl. ...................................... 424/81; 514/847; 514/873; 514/944
[58] Field of Search .......................................... 424/81

[56] References Cited

U.S. PATENT DOCUMENTS

| | | | |
|---|---|---|---|
| 3,697,644 | 10/1972 | Laiderman | 424/81 |
| 4,102,995 | 7/1978 | Hebborn | 424/81 |
| 4,246,285 | 1/1981 | Van Duzee | 424/326 |
| 4,294,823 | 10/1981 | Elliott et al. | 424/81 |
| 4,335,103 | 6/1982 | Barker et al. | 424/81 |
| 4,368,189 | 1/1983 | Mentlik | 424/81 |

OTHER PUBLICATIONS

Spec. Sheets for Lubrajel CG.
Trademark Registration No. 995,185, "Lubrajel".
Sagarin, *Cosmetic: Science & Technology*, pp. 99–181.
*Handbook of Nonprescription Drugs*, 6th ed., 1979, pp. 407–409.

*Primary Examiner*—Dale R. Ore

[57] ABSTRACT

A clear oil-free, non-greasy skin moisturizing composition is provided which includes as the major component a copolymer of glycerol and methacrylic acid, that is, polyglycerylmethacrylate together with a polyol to enhance skin feel, one or more preservatives and water, and optionally one or more thickeners, one or more skin soothing agents, such as allantoin and/or dl-panthenol, one or more astringents, and/or one or more colorants.

15 Claims, No Drawings

NOVEL CLEAR OIL-FREE MOISTURIZER COMPOSITION

REFERENCE TO OTHER APPLICATIONS

This application is a continuation-in-part of application Ser. No. 437,085, filed Oct. 27, 1982 now abandoned.

FIELD OF THE INVENTION

The present invention relates to a clear oil-free, and thus non-greasy non-petrolatum containing, skin moisturizing composition which contains as its major component a copolymer of glycerol and methylmethacrylate and is free of guanidine salts.

BACKGROUND OF THE INVENTION

Until now, most skin moisturizer compositions available to the average consumer have been formulated as creams and lotions which include an oil as a major ingredient. Such oil-containing skin moisturizers have enjoyed world-wide acceptance since they provide desired moisture to alleviate dry skin conditions. However, they impart a greasy sticky feel to the skin and are messy and stain clothing. Accordingly, a moisturizer composition which is effective in treating dry skin but which is not greasy to the touch would indeed be a welcomed improvement.

DESCRIPTION OF THE INVENTION

In accordance with the present invention an improved moisturizing composition is provided which is a clear, oil-free (and thus free of petrolatum) composition and therefore non-greasy to the skin and touch and includes as the major moisturizing component a copolymer of glycerol and methylmethacrylate also referred to herein as polyglycerylmethacrylate, one or more skin feel enhancers which is preferably a polyol and is not a guanidine salt, one or more preservatives, and water as the carrier. The moisturizer composition will also preferably include one or more thickeners, one or more skin conditioning agents, one or more astringents, and/or colorants and/or fragrances. The above moisturizing composition of the invention may be in the form of a clear lotion or gel. The above compositions of the invention are free of petrolatum and guanidine salts.

The major moisturizing component, namely, the polyglycerylmethacrylate is in the form of a white transparent gel containing from about 50 to about 75% by weight solids, and may or may not contain incidental ingredients, such as propylene glycol which may be present in an amount of 2% or less. A preferred polyglycerylmethacrylate is Lubrajel CG, a registered trademark of United Guardian Inc., which is distributed by Meadow Technical Corp., Livingston, N.J. The preferred form of Lubrajel has a viscosity at 20° C. (Brookfield RTV) ranging from about 400,000 to about 5,000,000, a specific gravity of 1.2 mg/ml, is completely soluble in water and is substantially stable at 250° F., and on sealed storage for 3 years at 20° C. Lubrajel CG is a clathrate formed by the reaction of glycerin and methylmethacrylate.

The polyglycerylmethacrylate will be present in the moisturizing composition in an amount within the range of from about 4 to about 50% and preferably from about 10 to about 25% by weight. The above polymer may be employed by itself or as a dispersion with other polyols, such as propylene glycol or any of the polyols mentioned hereinafter with respect to the skin feel enhancer.

The component for providing enhanced skin feel will preferably comprise a polyol which will be present in an amount within the range of from about 0.5 to about 20% and preferably from about 3 to about 10% by weight. Examples of such polyols (which also serve as humectants) suitable for use herein include, but are not limited to, polyethylene glycol (for example, PEG 8), sorbitol, glycerol, propylene glycol, 1,3-butylene glycol, hexylene glycol or polyoxyethylene 26 glycerine with glycerol and polyethylene glycol 8 (that is, made from 8 moles of ethylene oxide) being preferred.

The moisturizing composition of the invention will also include from about 0.05 to about 1.5% and preferably from about 0.1 to about 1% by weight of a preservative, such as imidazolidinyl urea (for example, Germall 115), methyl paraben, dimethyldimethoyl hydantoin, Dowicil 200 (Quaternium 15), that is, N-(3-chloroallyl)-hexaminium chloride, benzyl alcohol and/or phenoxyethanol, with imidazolidinyl urea and methyl paraben being preferred.

Water will be employed in the moisturizing composition of the invention as the primary solvent and carrier and will be present in an amount within the range of from about 50 to about 90% and preferably from about 60 to about 80% by weight.

The moisturizing composition of the invention will optionally include a thickener in an amount within the range of from about 0.05 to about 1% and preferably from about 0.05 to about 0.3% by weight. A preferred thickener suitable for use herein is Carbopol 940 or Carbomer 940 which is hydrophilic acrylic polymer cross-linked with a polyfunctional agent and employed with an organic or inorganic base, preferably triethanolamine. Other examples of thickeners which may be employed herein include, but are not limited to, hydroxyethyl cellulose, hydroxypropyl cellulose or xanthan gum.

Skin conditioning agents which may optionally be present in the moisturizing composition of the invention include allantoin, d- or dl-panthenol, hydrolyzed animal protein and the like. Such conditioning agents may be present in an amount within the range of from about 0.01 to about 5% and preferably from about 0.05 to about 2% by weight.

The astringents which may optionally be included will be present in an amount within the range of from about 1 to about 20% and preferably from about 3 to about 10% by weight of the moisturizing composition of the invention. Examples of such astringents suitable for use herein include ethanol and isopropyl alcohol.

The moisturizing composition of the invention may also be employed in formulating clear skin toners, after shave lotions, colognes, after-sun products and the like. Accordingly, such skin preparations may include, in addition to the ingredients set out above, certified water-soluble colorants as deemed necessary, fragrances in amounts within the range of from 0 to about 35% and preferably from about 0.1 to about 20% by weight depending upon the ultimate use of the skin preparation, solubilizing agents, such as polyoxyethylene (13) octylphenyl ether, polyoxyethylene 20 sorbitan laurate, polyoxyethylene 20 oleyl ether, and the like.

Preferred formulations within the scope of the present invention contain from about 10 to about 25% by weight polyglycerylmethacrylate (60 to 70% solids), from about 3 to about 10% by weight glycerol and/or polyethylene glycol, from about 0.1 to about 1% by weight imidazolidinyl urea and/or other preservatives, from about 60 to about 80% by weight water, optionally from about 0.05 to about 0.5% Carbomer 940 acrylic polymer, optionally from about 0.05 to about 2% by weight allantoin and/or panthenol, optionally from about 3 to about 20% by weight ethanol and/or isopropyl alcohol.

The skin preparations of the invention containing the moisturizing composition as set out above can be prepared as follows. Where the moisturizer composition is to be in the form of a clear lotion or gel, then all of the ingredients may be simply mixed together, preferably without heat, if possible, and then bottled.

The following examples represent preferred embodiments of the invention. All temperatures are expressed in degrees Centigrade.

EXAMPLE 1

A moisturizer composition in the form of a clear lotion in accordance with the present invention having the following composition was prepared as described below.

| Ingredient | Parts by Weight |
| --- | --- |
| Mix A | |
| dl-Panthenol | 0.5 |
| Allantoin | 0.5 |
| Germall 115 (imidazolidinyl urea) | 0.4 |
| Hydrolyzed animal protein | 0.5 |
| Mix B | |
| Carbowax 400 (PEG 8) | 2 |
| Tegasept M (methylparaben) | 0.2 |
| Polyglyceryl methacrylate (Lubrajel CG, 66% solids) | 10 |
| Ethanol | 5 |
| Deionized water | 81 |

The ingredients identified by Mix A were mixed together to form a first mixture, and the ingredients identified by Mix B were mixed together to form a second mixture. The two mixtures were then mixed together, without heat, to form the moisturizing composition of the invention.

The so-formed moisturizer composition was then packaged in bottles equipped with a non-aerosol pump dispenser and used as an intensive greaseless body spray.

EXAMPLE 2

A moisturizer composition in accordance with the present invention, which is useful as a skin moisturizer in the form of a clear lotion, was prepared as described below.

| Ingredient | Parts by Weight |
| --- | --- |
| Mix A | |
| Deionized water | 71.5 |
| Germall 115 (imidazolidinyl urea) | 0.4 |
| Allantoin | 0.5 |
| dl-Panthenol | 0.5 |
| Mix B | |
| Carbowax 400 (PEG 8) | 2 |
| Methylparaben | 0.2 |
| Component C | |
| RD & C red #4 (0.1%) | 0.1 |
| Component D | |
| Polyglycerylmethacrylate (Lubrajel CG) in propylene glycol (66% solids) | 25 |

The ingredients identified by Mix A were mixed together to form a first mixture and the ingredients identified by Mix B were mixed together to form a second mixture. The first mixture, the second mixture and Component C (Red 4) were mixed together at 50° C. until a clear solution was obtained and thereafter Component D (Lubrajel CG) was added with mixing for about 30 minutes until a uniform mixture was obtained.

The above moisturizing composition was found to be an excellent greaseless skin moisturizer.

EXAMPLE 3

A greaseless skin moisturizing composition in the form of a clear gel in accordance with the present invention having the following composition was prepared as described below.

| Ingredient | Parts by Weight |
| --- | --- |
| Mix A | |
| Deionized water | 63 |
| dl-Panthenol | 0.5 |
| Allantoin | 0.5 |
| Glydant (55% solids-dimethyl-dimethoyl hydantoin) | 0.3 |
| Mix B | |
| Carbowax 400 (PEG 8) | 3 |
| Methylparaben | 0.2 |
| Component C | |
| Lubrajel CG (polyglyceryl-methacrylate, 66% solids) | 16 |
| Component D | |
| 2% Carbopol 940 solution (acrylate polymer) | 15 |
| Mix E | |
| Deionized water | 1 |
| Triethanolamine (99%) | 0.3 |

The ingredients identified by Mix A were mixed together to form a first mixture and the ingredients identified by Mix B were mixed together to form a second mixture. Thereafter, the Mixes A and B were mixed together at ambient temperature and then each of the Components C, D and Mix E were separately added with mixing until a uniform mixture was obtained.

The resulting gel moisturizing composition was found to be an excellent greaseless skin moisturizer.

EXAMPLE 4

The following experiments were carried out to test moisturizer compositions containing polyglycerylmethacrylate in accordance with the present invention, also referred to as the "Invention", versus 100% petrolatum also referred to as the "Prior Art". Inasmuch as, "petrolatum is the unrivaled moisturizer" when it comes to efficacy, ("Regression method for assessing the efficacy of moisturizers", *Cosmetics and Toiletries*, Albert Kligman, 93:27, 1978), and since the formulation of the invention contains no petrolatum, the comparison of the formulation of the invention versus 100% petrolatum is the best possible comparison that can be made. A formulation with only 25% petrolatum employed in place of the 25% moisturizer in the Example 4 formulation would not be as good a moisturizer as a composition formed of 100% petrolatum.

PROCEDURE

Twenty volunteers with moderate to severe xerosis (dry skin) were selected for participation in this study. All volunteers completing the study were healthy (as determined by medical history), female Caucasians, ranging in age from 35 to 48 years (mean, 39.7 years).

The method employed in this study was developed by Dr. Albert Kligman and is described in the Kligman paper, supra. Dr. Kligman, a world reknown dermatologist, indicates in his paper, that "petrolatum is the unrivalled moisturizer. No material in our experience exceeds it in relieving xerosis . . . . It is very useful as a benchmark to the experimenter."

Approximately 1.0 ml of the product moisturizer composition containing polyglycerylmethacrylate as described below (invention in Table A) and prepared as described in Example 1 of the subject patent application was applied twice daily to the front half of one lower leg, between the knee and ankle of ten volunteers, and rubbed in for 15 seconds. Applications were made in this manner Monday through Friday for three weeks. The other leg was not treated and served as a control.

Ten other volunteers were treated in a similar manner as described above except that one leg was treated with 100% petrolatum and the other leg was not treated.

Dryness was evaluated according to the scale presented below on enrollment (prior to initiating product use, Day 1) and on subsequent Monday mornings prior to application of the product (Days 8 and 15). Additional evaluations were made on Days 22, 25, 29 and 33 (3, 6, 10 and 14 days, respectively, after product use was discontinued).

0 = Normal, hydrated skin
+1 = Dry appearance, minor flaking
+2 = Many loose flakes, no fissuring present
+3 = Many loose flakes, fissuring

TABLE A

MOISTURIZER FORMULATIONS TESTED

| | Parts by Weight | |
| --- | --- | --- |
| Ingredient | Example 4 Invention | Prior art |
| Deionized water | 71 | |
| Imidazolidinyl urea | 0.4 | |
| Sodium ethylenediaminetetra-acetic acid | 0.01 | |
| Allantoin | 0.5 | |
| DL-Panthenol | 0.5 | |
| Carbowax 400 (PEG 8) | 2 | |
| TegM (methyl paraben) | 0.15 | |
| Color | 0.1 | |
| Polyglycerylmethacrylate (Lubrajel) | 25 | |
| Petrolatum | 0 | 100 |

There were no restrictions in this study as to methods of personal hygiene and bathing, except that the use of Ivory Soap or rubbing alcohol was strictly prohibited.

Student's paired t-test was used to compare the mean control and treatment scores at each of the aforementioned observation days.

Results

The percent (%) skin improvement over the control (untreated) obtained in using the Example 4 formulation containing the polyglycerylmethacrylate ("Invention") for days 8, 15, 22, 25, 29 and 33 and the percent (%) skin improvement over the control (untreated) obtained in using 100% petrolatum ("Prior Art") for days 8, 15, 22, 25, 29 and 33 are set out in Table B below.

The " % skin improvement" as shown in Table B is an average score according to the above dryness scale of the ten volunteers treated with the "Invention" and an average score according to the above dryness scale of the ten volunteers treated with the "Prior Art" (petrolatum). The " % skin improvement" for each day shown is obtained by evaluating the treated leg and the untreated leg of each of the ten volunteers of each of the "Invention" and "Prior Art" groups, and assigning a numerical value according to the above scale for each evaluation.

% skin improvement for each day for each volunteer is obtained as follows:

$$\frac{\text{Control Leg Score} - \text{Treated Leg Score}}{\text{Control Leg Score}} \times 100$$

TABLE B

| | % Skin Improvement | | | | | |
| --- | --- | --- | --- | --- | --- | --- |
| Day (after initial application) | 8 | 15 | 22 | 25 | 29 | 33 |
| Moisturizer composition containing polyglyceryl-methacrylate (Invention) Average % skin improvement over control | 67.9 | 64 | 76.9 | 57.7 | 57.7 | 53.9 |
| Petrolatum (Prior Art) Average % skin improvement over control | 47 | 53 | 72 | 57 | 40 | 35 |

The actual % skin improvement of the "Invention" over the "Prior Art" is set out in Table C below and was calculated as follows.

$$\frac{\substack{\text{Average \% skin} \\ \text{improvement of} \\ \text{Invention over} \\ \text{control}} - \substack{\text{Average \% skin} \\ \text{improvement of} \\ \text{Prior Art over} \\ \text{control}}}{\text{Average \% skin improvement of Prior Art over control}} \times 100$$

TABLE C

| | % Skin Improvement of Invention over Prior Art | | | | | |
| --- | --- | --- | --- | --- | --- | --- |
| Day (after initial application) | 8 | 15 | 22 | 25 | 29 | 33 |
| % Skin improvement of Invention over Prior Art | 44.5% | 20.4% | 6.75% | 1.3% | 44% | 54% |

As seen from the results shown in Tables B and C, during the application period, Days 8 and 15, the "Invention" moisturizer was surprisingly superior to the "Prior Art" petroleum, that is, 44.5% (Day 8) and 20.4% (Day 15) increase in % skin improvement of "Invention" over "Prior Art".

However, the essential and key feature of a moisturizer is its lasting quality (in regression) in inhibiting onset of dry skin after use of the moisturizer has been discontinued. Several days after terminating application of moisturizer (at Day 21), upper layers of skin (stratum cornum) containing moisturizer slough off; the result is an initial dramatic increase in skin dryness (compare results of Days 22 and 25 in Tables B and C, that is, 1 or 4 days after terminating application). However, at Day 29 (8 days after terminating application), the moisturizing action of the "Invention" moisturizer has stabilized (57.7% at Day 25→57.7% at Day 29) while the staying power of the "Prior Art" petrolatum has dramatically declined (57% at Day 25→40% at Day 29). Thus, at Day 29 the results show that the "Invention" is 44% superior in moisturizing dry skin as compared to the "Prior Art" petrolatum. The results shown for Day 33 (12 days after terminating application) further shows that the "Invention" has a lasting residual quality which is very much superior to (54% greater) than the lasting residual quality of the "Prior Art" petrolatum. In fact, the results show that the moisturizer of the "Invention" is surprisingly superior to the "Prior Art" petrolatum in retarding formation of dry skin.

As seen from Tables B and C, the moisturizer composition of the invention containing polyglycerylmethacrylate was significantly and substantially superior to the prior art 100% petrolatum composition in treating dry skin.

During the application period, Days 8 and 15, the "Invention" moisturizer was surprisingly superior to the "Prior Art" petrolatum, that is, 44.5% (Day 8) and 20.4% (Day 15) increase in % skin improvement of "Invention" over "Prior Art".

However, as indicated in the Kligman article, supra, the essential and key feature of a moisturizer is its lasting quality (in regression) in inhibiting onset of dry skin after use of the moisturizer has been discontinued. Several days after terminating application of moisturizer (at Day 21), upper layers of skin (stratum cornum) containing moisturizer slough off; the result is an initial dramatic increase in skin dryness (compare results of Days 22 and 25 in Tables B and C, that is, 1 or 4 days after terminating application). However, at Day 29 (8 days after terminating application), the moisturizing action of the "Invention" moisturizer has stabilized (57.7% at Day 25→57.7% at Day 29) while the staying power of the "Prior Art" petrolatum has dramatically declined (57% at Day 25→40% at Day 29). Thus, at Day 29 the results show the "Invention" is 44% superior in moisturizing dry skin as compared to the "Prior Art" petrolatum. The results shown for Day 33 (12 days after terminating application) further shows that the "Invention" has a lasting residual quality which is very much superior to (54% greater) than the lasting residual quality of the "Prior Art" petrolatum. The results show that the moisturizer of the 'Invention' is surprisingly superior to the "Prior Art" petrolatum in retarding formation of dry skin.

What is claimed is:

1. A cosmetically acceptable oil-free non-greasy clear moisturizer composition which consists essentially of polyglycerylmethacrylate in an amount within the range of from about 4 to about 50% by weight of the composition to provide moisturizer properties to the composition, at least an effective amount of at least one non-guanidine containing skin feel enhancer which is a polyol, in an amount within the range of from about 0.5 to about 20% by weight, at least an effective amount of at least one preservative and water in an amount within the range of from about 50 to about 90% by weight of the composition, said moisturizing composition being in the form of a clear lotion or gel, free of petrolatum and guanidine salts.

2. The composition as defined in claim 1 further including at least one thickener in an amount within the range of from about 0.05 to about 1% by weight of the composition.

3. The composition as defined in claim 1 further including at least one skin conditioning agent in an amount within the range of from about 0.01 to about 5% by weight of the composition.

4. The composition as defined in claim 1 further including at least one alcohol astringent in an amount within the range of from about 1 to about 20% by weight of the composition.

5. The composition as defined in claim 1 further including at least one thickener, at least one skin conditioning agent, at least one astringent and optionally at least one fragrance.

6. The composition as defined in claim 1 wherein the polyglycerylmethacrylate is present in an amount within the range of from about 10 to about 25% by weight of the composition.

7. The composition as defined in claim 1 wherein the polyol is polyethylene glycol, sorbitol, glycerol, propylene glycol, 1,3-butylene glycol, hexylene glycol, or polyoxyethylene 26 glycerine, or mixtures of at least two thereof.

8. The composition as defined in claim 1 wherein the preservative is present in an amount within the range of from about 0.05 to about 1.5%.

9. The composition as defined in claim 8 wherein the preservative is imidazolidinyl urea, methyl paraben, dimethyl dimethoyl hydantoin, N-(3-chloroallyl) hexaminium chloride, benzyl alcohol, phenoxyethanol or mixtures of at least two thereof.

10. The composition as defined in claim 1 wherein the water is present in an amount within the range of from about 60 to about 80% by weight of the composition.

11. The composition as defined in claim 3 wherein the skin conditioning agent is allantoin, panthenol or mixtures thereof.

12. The composition as defined in claim 1 wherein the polyglycerylmethacrylate is dispersed in a polyol to provide from about 50 to about 75% solids.

13. The composition as defined in claim 1 consisting essentially of from about 6 to about 15% by weight polyglycerylmethacrylate, from about 3 to about 10% by weight propylene glycol, glycerol, polyethylene glycol, sorbitol or mixtures thereof, from about 0.1 to about 1% by weight imidazolidinyl urea or other preservatives, from about 60% to about 80% by weight water, optionally from about 0.05 to about 1% acrylic thickener, optionally from about 0.05 to about 2% by weight allantoin or panthenol or mixtures thereof, optionally from about 3 to about 10% by weight ethanol or isopropyl alcohol or mixtures thereof, all of the above % being based on the weight of the composition.

14. The composition as defined in claim 1 in the form of a transparent lotion.

15. The composition as defined in claim 1 in the form of a transparent gel.

* * * * *

UNITED STATES PATENT AND TRADEMARK OFFICE
CERTIFICATE OF CORRECTION

PATENT NO. : 4,863,725

DATED : September 5, 1989

INVENTOR(S) : Deckner et al.

It is certified that error appears in the above-identified patent and that said Letters Patent is hereby corrected as shown below: Title page:

Between "Inventors" and "Appln. No.", insert --Assignee: Charles of the Ritz Group Ltd.--

Signed and Sealed this

Fourth Day of September, 1990

Attest:

HARRY F. MANBECK, JR.

*Attesting Officer*  *Commissioner of Patents and Trademarks*